(12) United States Patent
Sarradon

(10) Patent No.: US 9,517,064 B2
(45) Date of Patent: Dec. 13, 2016

(54) CLIPS FOR VASCULAR ANASTOMOSIS AND METHOD OF USE

(76) Inventor: Pierre Sarradon, Toulon (FR)

( * ) Notice: Subject to any disclaimer, the term of this patent is extended or adjusted under 35 U.S.C. 154(b) by 66 days.

(21) Appl. No.: 13/129,708

(22) PCT Filed: Nov. 16, 2009

(86) PCT No.: PCT/FR2009/001310
§ 371 (c)(1),
(2), (4) Date: May 17, 2011

(87) PCT Pub. No.: WO2010/055232
PCT Pub. Date: May 20, 2010

(65) Prior Publication Data
US 2011/0230900 A1    Sep. 22, 2011

(30) Foreign Application Priority Data
Nov. 17, 2008   (FR) ..................... 08 06418

(51) Int. Cl.
*A61B 17/08*   (2006.01)
*A61B 17/064*   (2006.01)
*A61B 17/115*   (2006.01)
*A61B 17/00*   (2006.01)

(52) U.S. Cl.
CPC ....... *A61B 17/0644* (2013.01); *A61B 17/1152* (2013.01); *A61B 2017/00867* (2013.01)

(58) Field of Classification Search
CPC ... A61B 17/12; A61B 17/064; A61B 17/1222; A61B 17/1285; A61B 17/122; A61B 2017/07235; A61B 17/0682; A61B 17/1152; A61B 17/0644
USPC .............. 606/151–156, 219; 227/175.1
See application file for complete search history.

(56) References Cited

U.S. PATENT DOCUMENTS 2,557,448 A    5/1986   Kirsch et al.
4,610,251 A *  9/1986   Kumar ..................... 606/219
4,733,664 A    3/1988   Kirsch et al.
(Continued)

FOREIGN PATENT DOCUMENTS

EP    0 656 191 A    6/1995
EP    1 462 061 A    9/2004
(Continued)

*Primary Examiner* — Gregory Anderson
*Assistant Examiner* — Christina Lauer
(74) *Attorney, Agent, or Firm* — Frommer Lawrence & Haug LLP

(57) ABSTRACT

Disclosed is a surgical clip for end-to-end or end-to-side vascular anastomosis and for suturing blood conduits, which comprises a V-shaped base from which at least two branches project in a direction opposed to an apex of the V-shaped base. The branches each have a hook pointing toward the base, the branches are parallel to one another before plastic deformation and each branch forms with the corresponding hook a re-entrant corner with an apex angle of between 30° and 80°. The clip has three zones of preferential deformation, at an the apex of the V-shaped base and at connecting zones between the base and the branches. After plastic deformation, the two branches remain substantially parallel. The deformation of the clip has been concentrated on the apex of the base, the angle of which has narrowed under the stress of the gripper, and on the apices, which have opened.

8 Claims, 2 Drawing Sheets

(56) References Cited

U.S. PATENT DOCUMENTS

| | | | | |
|---|---|---|---|---|
| 4,841,960 A | * | 6/1989 | Garner | A61B 17/0642 |
| | | | | 606/216 |
| 4,844,066 A | * | 7/1989 | Stein | 606/158 |
| 5,171,253 A | * | 12/1992 | Klieman | 606/158 |
| 5,501,693 A | * | 3/1996 | Gravener | 606/157 |
| 2004/0193189 A1 | * | 9/2004 | Kortenbach et al. | 606/151 |
| 2006/0235468 A1 | * | 10/2006 | Huitema | A61B 17/064 |
| | | | | 606/219 |
| 2008/0173693 A1 | * | 7/2008 | Mas et al. | 227/175.1 |
| 2008/0312670 A1 | * | 12/2008 | Lutze et al. | 606/157 |

FOREIGN PATENT DOCUMENTS

| | | |
|---|---|---|
| EP | 1 712 186 A | 10/2006 |
| FR | 2 557 448 A | 7/1985 |
| FR | 2 588 467 A | 4/1987 |
| FR | 2 899 113 A | 10/2007 |
| WO | WO 03/099139 A | 12/2003 |

\* cited by examiner

CLIPS FOR VASCULAR ANASTOMOSIS AND METHOD OF USE

This application is a 371 of PCT/FR2009/001310 filed on Nov. 16, 2009, published on May 20, 2010 under publication number WO 2010/055232 A, and claims priority benefits to French patent application number 08 06418 filed Nov. 17, 2008 the entire disclosure of which is incorporated herein by reference.

TECHNICAL FIELD OF THE INVENTION

The present invention relates to the field of surgery and more particularly to the field of vascular surgery and, without limitation, to the field of vascular microsurgery performed on humans and animals.

PRIOR ART

In many surgical procedures, it is necessary to join blood vessels end to end. The procedure of connecting blood conduits, such as vessels, prostheses or grafts, brought into communication with one another is known by the term vascular anastomosis.

Until recently, vascular anastomosis was performed exclusively by suturing with a needle and thread. However, this procedure using a needle and thread is lengthy and awkward for the surgeon. In addition, this technique, which requires perforating the wall of the vessels at the points of penetration of the needle, is not entirely devoid of risk or of potentially damaging effects.

In the past few years, therefore, arterial surgery has seen the increasing use of vascular suturing clips, surgical grippers and micro-grippers, similar to those disclosed, for example, in the patent applications EP 1 712 186, FR 2 557 448 and FR 2 588 467. These clips, having what is generally a U shape, are composed principally of two branches that are able to grip around connected blood tissues, in order to keep these tissues together. Vascular clips of this type avoid the formation of clots in the vessels, because they do not pass through the tissues. Moreover, the placement of the clips can be simplified by the use of a dispensing gripper as described, for example, in the document EP 0 656 191, such that the clip application saves the surgeon time on the whole. However, the vascular anastomosis clips are used only on small vessels, the reason being that the pressure is too high in vessels of large diameter, and in particular in the principal arteries, and therefore the known clips are unable to keep the vessels joined together in the long term. Cases have also been observed clinically in which the clips slide and eventually come completely free, with a concomitant risk of the join opening and of hemorrhage.

Systems involving staples have also been known of for some years and are used, for example, for intestinal anastomoses. These penetrating staples withstand higher pressure. However, if they were to be applied to blood vessels, they would require perforation of the vessel wall and would involve a metal part being maintained inside the vessel, which could lead to platelet aggregation and possible local thickening of the walls of the vessels and narrowing of the internal lumen of the vessels, or even the formation of clots. Moreover, the perforation would entail a risk of tearing of the vessels.

SUBJECT MATTER OF THE INVENTION

The present invention is intended to overcome the disadvantages of the prior art by making available a surgical clip permitting vascular anastomosis in humans or animals, in particular vascular anastomosis of blood conduits of any diameter, particularly those of large diameter, in particular the principal arteries, which vascular anastomosis is quick and long-lasting and limits as far as possible the problems of platelet aggregation, thickening of the vessels, reduction in the cross section of the blood conduit, or formation of clots in the blood conduits. In the present application, blood conduit is understood as meaning the blood vessels and also vascular prostheses and grafts.

Moreover, the device according to the invention not only permits vascular anastomosis, it also permits the suturing of blood conduits.

To this end, the present invention proposes using a surgical clip with plastic deformation or with shape memory, comprising a base from which at least two branches project, each branch having a hook pointing toward the base. These hooks permit anchoring of the clip in the vessel walls that are to be sutured, but without perforating said vessel walls, so as to ensure that the clip is held in place, even in the presence of high arterial pressures, as is the case in the vessels of large diameter. The deformation of the clip, whether obtained plastically or by the memory effect of a shape-memory alloy, permits a sufficient hold of the tissues. Such a hold could not be obtained, for example, by elastic deformation of the clip and of the tissues.

In a particular embodiment of the present invention, the base is deformable plastically or by a memory effect in order to bring the branches of the clip closer together, in such a way that the hooks plant themselves in the vessel walls that are to be joined, but without perforating the vessel walls.

Each branch preferably forms, with its hook, a re-entrant corner with an apex angle of between 30° and 80°. These angles permit good engagement and good anchoring of the hooks in the tissues.

The free ends of the branches can advantageously be rounded in order to avoid physiological damage to the tissues.

According to one embodiment of the invention, the branches of the clip before deformation are parallel.

The base can advantageously form a V shape deformable at its apex, such that the clip has three zones of preferential deformation, namely the apex and the connecting zones between the base and the branches.

According to one embodiment, the clip has two parallel plane faces, which each cover the base and the two branches, and the two plane faces are spaced apart from each other by a distance P of between 0.5 and 3 mm and, preferably, of less than 1.5 mm. It is thus possible to store the clips in a stack forming small bars that can be inserted into a dispensing gripper.

The clip has a height H, measured parallel to the parallel plane faces, which is preferably between 1 and 5 mm. Each hook has a free end situated at a distance E from the internal face of the branch to which this hook is connected, this distance E advantageously verifying the inequality:

$0.05 \times H < E < 0.4 \times H$ and, preferably, $0.1 \times H < E < 0.3 \times H$.

Advantageously, the thickness P of the clip is such that $0.1 \times H < P < 0.4 \times H$.

Moreover, the clip according to the present invention is made of a biocompatible material which, according to a preferred embodiment, can be titanium, so as to be tolerated by the human body.

Alternatively, a shape-memory alloy, especially a nitinol, as described in the document FR 2 899 113, for example.

The clip is advantageously made all in one piece in order to facilitate its production.

The clip can be used in particular for end-to-end, side-to-end and side-to-side anastomoses, for lateral sutures and for application of patches.

The present invention also relates to a method of end-to-end vascular anastomosis between a first blood conduit and a second blood conduit, wherein it comprises the following steps:
- partially turning back an end wall of the first blood conduit;
- inserting the turned-back end of the first conduit into an end wall of the second blood conduit in order to form a continuous join between the two end walls;
- positioning a clip with two branches astride the two ends at one point of the join, each branch having a rounded free end and a hook on the internal face of each of the branches;
- closing said clip by plastic deformation or by a memory effect, in such a way that the hooks anchor themselves in the end walls of the two blood conduits, but without passing through the walls;
- repeating the positioning and closing maneuvers across the whole join.

The invention also relates to a method of end-to-side vascular anastomosis between an end wall of a first blood conduit and a side wall of a second blood conduit, wherein it comprises the following steps:
- partially turning back the end wall of the first blood conduit;
- making an incision in the side wall of the second blood conduit;
- inserting the turned-back end wall of the first conduit into the incision in the side wall of the second blood conduit in order to form a join between the walls;
- positioning a clip with two branches astride the turned-back end wall and an edge of the incision, each branch having a rounded free end and a hook on the internal face of each of the branches;
- closing said clip by plastic deformation or by a memory effect, in such a way that the hooks anchor themselves in the walls, but without passing through the walls;
- repeating the positioning and closing maneuvers across the whole join.

The blood conduits in question can include vessels, prostheses or grafts.

According to a particular embodiment, the clips are arranged all around the periphery of the join, with a spacing of one millimeter between them.

BRIEF DESCRIPTION OF THE FIGURES

Other features and advantages of the invention will become clear from the following description and by reference to the attached figures, in which.

ILLUSTRATIVE EMBODIMENT

Figure 1:
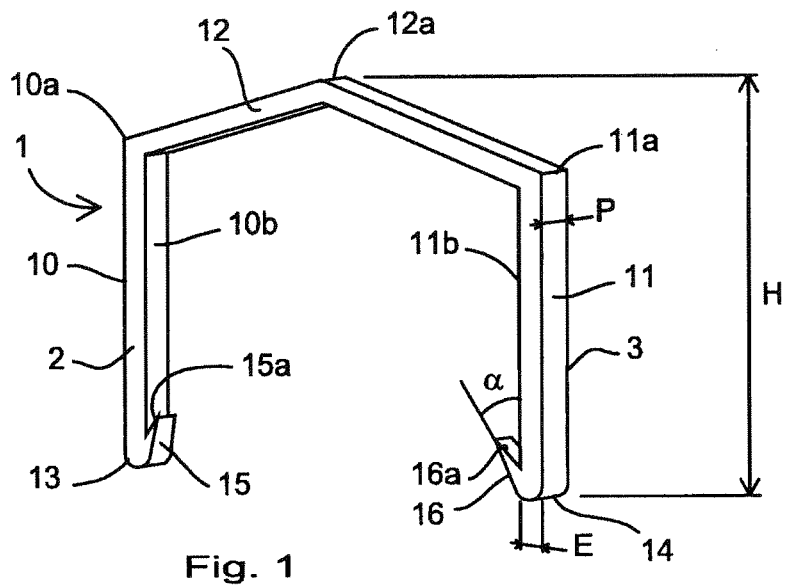
FIG. 1 shows a perspective view of a surgical clip according to a first embodiment of the present invention, in an initial position in which it is not deformed.

Referring to FIG. 1, a surgical clip 1 according to the invention is all in one piece and is made from a biocompatible and plastically deformable material, for example titanium. The clip is formed in a flat plate, for example by laser cutting or by electrochemical cutting, and for this reason has two parallel plane faces 2, 3, and the distance between these faces determines the constant thickness P of the clip.

The clip has two parallel end branches 10 and 11, which are interconnected by a base 12 forming a V shape with apex 12a. The free ends 13 and 14 of the two branches are rounded in order to avoid any tearing of the tissues and any clot formation. Two hooks 15, 16, forming an integral part of the branches 10, 11, point toward each other and toward the base 12. The end of each of the hooks 15 and 16 is preferably ridge-shaped. The branches form an open angle of apex 10a, 11a with the base 12. Notably, each hook has a face 15a, 16a directed toward the internal face 10b, 11b of the corresponding branch and forming a re-entrant corner of re-entrant angle α.

The dimensions of the clip vary depending on the size of the blood conduits for which it is designed. The thickness P of the clip is of the order of 0.5 to 1.5 mm. The height H of the clip, measured between the apex 12a and a plane that is perpendicular to the plane of the clip and joins the free ends 13, 14, thus varies between 2 and 5 mm. The distance E between the free end of the hook and the internal face of the corresponding branch varies between 0.1 and 0.3 times H. The acute angle α is always less than 90° and varies preferably between 30° and 60° or 80°.

Figure 2:
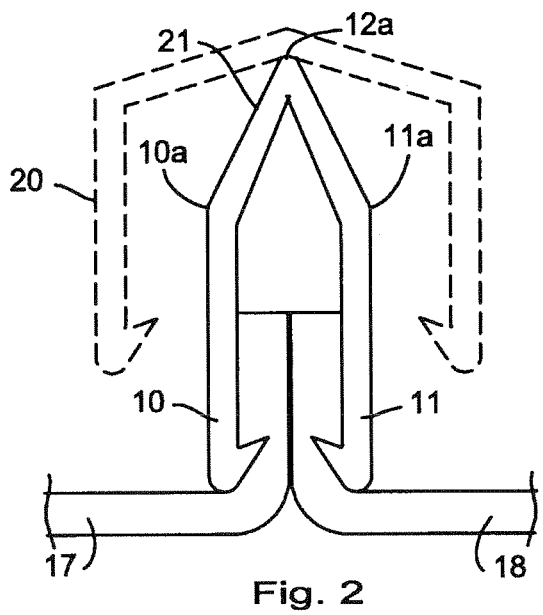
FIG. 2 shows a sectional view of the clip from FIG. 1, pinched for end-to-end suturing of two vessels.

FIG. 2 shows the same clip 20 in broken lines before plastic deformation. This figure also shows, in solid lines, this same clip 21, which grips two tissues 17 and 18 after plastic deformation of the clip. The clip has been placed astride the two tissues and has then been tightened around the tissues by plastic deformation, in such a way that the hooks 15, 16 anchor themselves in the tissues, but without passing through the tissues. After plastic deformation, the two branches 10 and 11 of the clip remain substantially parallel. The deformation of the clip has been concentrated on the apex 12a of the base, the angle of which has narrowed under the stress of the gripper, and on the apices 10a, 11a, which have opened.

The hooks, directed toward the base of the clip, have anchored themselves in the tissues, without passing through the latter, and they anchor the clip in a way that prevents the tissues from sliding out of the clip, even in the presence of a high blood pressure or in the event of external mechanical stress.

To fit the clip in place in an end-to-end anastomosis, the following procedure is performed. In a first step, the ends of two blood conduits are brought together using suitable means, one of the ends being everted, that is to say turned back externally. A clip, held in a clip gripper, is positioned astride a point of contact of the tissues of these blood conduits intended to form the join between the blood conduits. The gripper then allows the clip to be placed tightly round the tissues of the blood conduits, in such a way that the branches of the clip are moved closer together in parallel around the tissues, and in such a way that the hooks anchor themselves in the tissues, but without perforating the latter. This tightening is achieved by plastic deformation of the base with the aid of the gripper or of any other means allowing the clip to be tightened. The deformation of the apices 10a and 11a is induced by the resistance of the tissues. The plastic deformation of the clip is permanent. This maneuver is repeated at as many points as is necessary in order to join the chosen tissues. The deformation of the base allows the clip to hold the tissues together without perforating them. Moreover, the hooks prevent the tissues from sliding in the clip, even in the presence of high pressures, as is the case in the large blood vessels. Moreover, these hooks do not perforate the tissues, and therefore they avoid the formation of clots in the vessels.

The maneuver is repeated about the entire periphery of the join between the two tissues. Traction is then exerted on the conduits in such a way as to open out the previously turned-back end of the blood conduit and to test the strength of the join that has been made.

The procedure is performed analogously for side-to-end or side-to-side anastomoses.

These clips thus afford a quick way of suturing tissues and are easier for the surgeon to apply than the conventional procedures, for example suturing with needle and thread. These clips also allow anastomoses to be performed on all types of blood vessels, including the largest ones, and avoid the disadvantages of the other techniques.

Many variations are of course possible. The base can, for example, be shaped as an arc of a circle. It is also conceivable to have a clip with a square, rectangular or even round cross section, depending on the methods of production of the clip and on the materials from which it is made. Moreover, the clip can have more than two branches, for example 5 branches arranged in a circle around the base, which makes it possible, for example, to close the end of a vessel. Moreover, it is conceivable for the clip to be made of any biocompatible material, including a polymer, on condition that the chosen material is plastically deformable and is sufficiently ductile to maintain its shape when the clip is in the tightened position.

Figure 3:
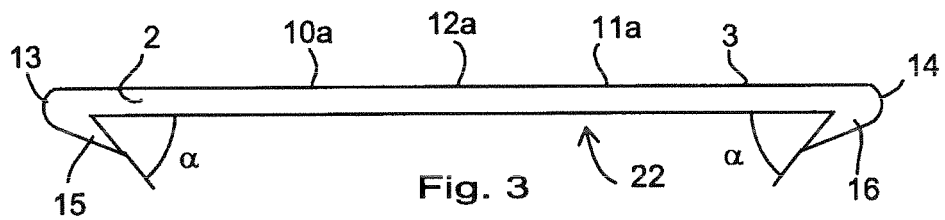
FIG. 3 shows a front view of a metal wire used to produce a surgical clip with shape memory.

According to another variant, the clip can be made of a shape-memory alloy, with a one-way effect based on nickel, for example the alloy known by the trade name Nitinol. The clip is produced starting from a linear metal wire with a square cross section and with a thickness of between 0.3 and 1.5 mm, similar to that shown in FIG. 3. At each of its ends, this wire comprises a hook 15 or 16 forming an acute angle with the linear wire. The two ends 13 and 14 of the wire are rounded so as not to damage the tissues, such that the clip has an initial shape analogous to that shown in FIGS. 1 and 2.

Starting out from the wire 22, the clip is first of all shaped by mechanical deformation of the points 10a, 11a and 12a at a high temperature close to 700° C., such that it assumes its initial shape 20.

The clip is then trained to remember its locking shape 21. This memorization is achieved by mechanical deformation and simultaneous heating at a temperature close to 700° C. The clip is heated particularly in the area of its apices 10a, 11a and 12a, which are deformed such that the clip assumes its final shape 21.

The clip is then abruptly cooled by plunging it in a cold bath at a temperature of between about −26° C. and +20° C., so as to stop the training as per the shape 21. The clip is then in its locked position 21.

A first heat treatment is then carried out at a temperature close to 600° C. The heating lasts for less than 10 minutes. A second heat treatment is then carried out at a temperature close to 300° C. This second heat treatment step lasts for about 10 minutes.

A layer of a biocompatible material such as titanium is then deposited on the clip, and the clip is returned to its initial position 20 by mechanical deformation effected at a temperature of between 18 and 25° C.

This process of training the clip is known from the prior art and is described in more detail in the document FR 2 899 113.

Of course, other methods can be used to produce the clip, and this one is given only by way of illustration.

Thus, when the clip is at a temperature of between 20 and 35° C., it remains in its initial configuration 20. Then, when applying the clip, the surgeon places the clip around the tissues that are to be joined, as in the preceding embodiment, and, when the clip is at a temperature of greater than or equal to 35° C., it recovers its locking shape 21, in which it holds the tissues together, as in the preceding embodiment.

The use of a clip made of a shape-memory alloy makes it possible to tighten the clip always in the same manner, which is not always the case when the clip is tightened mechanically. Thus, the tightening of the clip and the positioning of the hooks in the tissues to be joined are more precise and more regular.

It is also conceivable to use two-way shape-memory alloys, which are able to remember two configurations, in particular a configuration permitting extraction of the clip. It is also conceivable to tighten the clip around the tissues by mechanical deformation, as in the above example, and, under the effect of temperature, the clip will maintain its locking position 21, thereby countering the opening of the clip and the sliding of the tissues.

Figure 4:
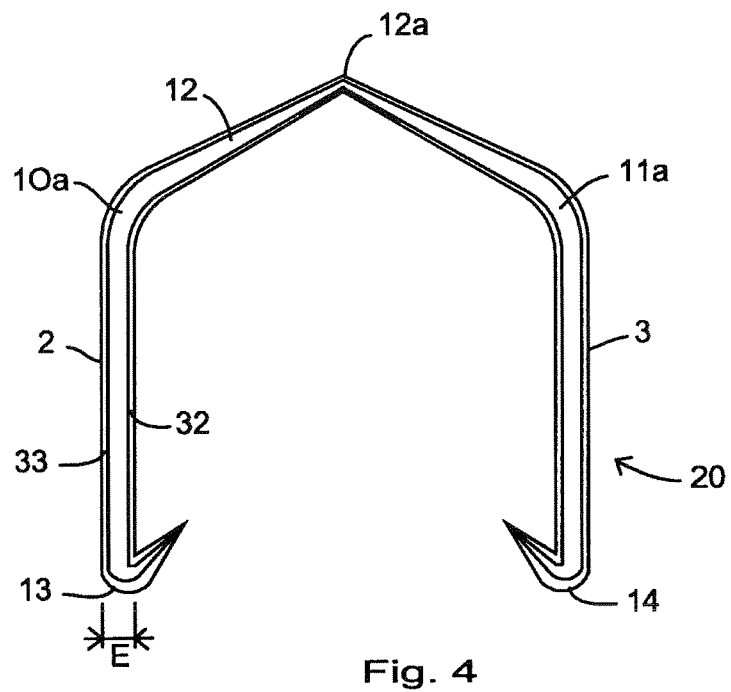
FIG. 4 shows a front view of a surgical clip according to a second embodiment of the present invention, in its initial and undeformed position.
Figure 5:
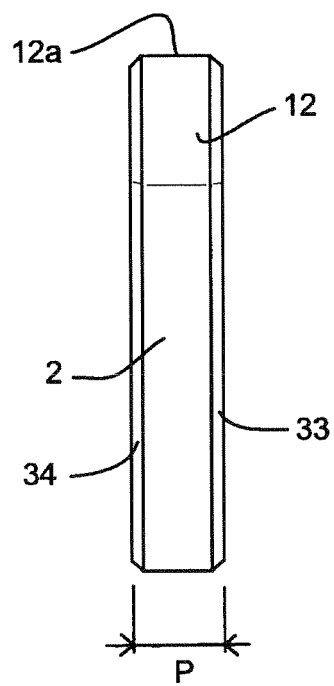
FIG. 5 shows a side view of a surgical clip according to the embodiment in FIG. 4, and more particularly a view of the branch 2.
Figure 6:
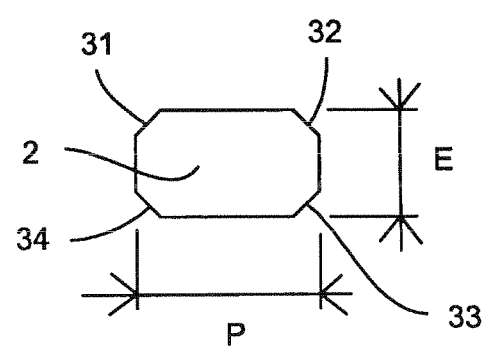
FIG. 6 shows a view of the cross section of the clip according to the embodiment in FIG. 4.

Other embodiments are of course possible. Thus, FIGS. 4, 5 and 6 show another embodiment of the present invention, one in which the cross section of the clip is rectangular with sides E and P. The edges 31, 32, 33 and 34 of the clip 20 are beveled, by which means it is possible to avoid damage to the tissues by the edges of the clip. For the same reason, the apices 10a and 11a are rounded. Moreover, in this embodiment, the base 12 is thinner at the apex 12a, in order to facilitate the deformation of the clip.

The invention claimed is:

1. A plastically deformable surgical clip for end-to-end or end-to-side vascular anastomosis of blood conduits and for suturing blood conduits, made in one-piece of biocompatible material, consisting essentially of
   a V-shaped base and of two straight branches which project from the V-shaped base in a direction opposed to an apex of the V-shaped base wherein the branches are parallel to one another before plastic deformation, and join the V-shape base at connecting zones at an obtuse angle such that a sum of the obtuse angle of each of the connecting zone and of an angle of the apex of the V-shaped base is substantially 360°,
   wherein the branches each have an internal face and at least one corresponding hook protruding from the internal face at a distance from the internal face and pointing toward the base for penetrating walls of the blood conduits without perforating said walls, and
   each branch forms with the corresponding hook a re-entrant corner with an apex angle of between 30° and 80°,
   wherein the clip has three zones of preferential plastic deformation, at the apex of the V-shaped base and at connecting zones between the base and the branches, whereby the clip is plastically deformed by narrowing the apex of the V-shaped base and bringing closer to one another and opening the connecting zones between the base and the branches such that the two branches are brought closer to one another and remain substantially parallel after deformation, wherein the clip is entirely contained between two parallel geometrical planes, each of which contains one end face of the clip, wherein the end face covers the base and the two branches, wherein the internal face of each of the branches is planar and extends between the V-shaped base and the corresponding hook.

2. The clip of claim 1, wherein the clip is made of titanium.

3. The surgical clip of claim 1, wherein the two parallel planar end faces are spaced apart from each other by a distance P of between 0.5 and 1.5 mm.

4. The clip of claim 3, wherein each of the two branches has a free end and the clip has a height H, measured between the apex and a plane crossing the free end of each of the two branches and perpendicular to the parallel plane faces, of between 1 and 5 mm.

5. The clip of claim 3, wherein each of the two branches has a free end and the clip has a height H, measured between the apex and a plane crossing the free end of each of the two branches and perpendicular to the parallel planar end faces and the distance P is such that $0.1 \times H < P < 0.4 \times H.$ 6. The clip of claim 1, wherein each of the two branches has a free end, and the two planar end faces are spaced apart from each other by a distance P of between 0.5 and 3 mm, the clip having a height H, measured between the apex and a plane crossing the free end of each of the two branches and perpendicular to the parallel planar end faces, such that:

$0.05 \times H < E < 0.4 \times H$ where E is the distance between the free end of each hook and an internal face of the branch to which the hook is connected.

7. A plastically deformable surgical clip for end-to-end or end-to-side vascular anastomosis of blood conduits and for suturing blood conduits, made in one-piece of biocompatible material, consisting essentially of a V-shaped base and of two branches which project from the V-shaped base in a direction opposed to an apex of the V-shaped base, wherein the branches each have an internal face and a free end provided with a corresponding hook protruding from the internal face at a distance from the internal face and pointing toward the base for penetrating walls of the blood conduits without perforating said walls, the branches are parallel to one another before plastic deformation and each branch forms with the corresponding hook a re-entrant corner with an apex angle of between 30° and 80°, wherein the clip has three zones of preferential plastic deformation, at the apex of the V-shaped base and at connecting zones between the base and the branches, whereby the clip is plastically deformed by narrowing the apex of the V-shaped base and bringing closer to one another and opening the connecting zones between the base and the branches such that the two branches are brought closer to one another and remain substantially parallel after deformation, wherein the clip is entirely contained between two parallel geometrical planes, each of which contains one end face of the clip, wherein the end face covers the base and the two branches, wherein the internal face of each of the branches is planar and extends between the V-shaped base and the corresponding hook, wherein before deformation, a sum of an angle at the apex of the V-shaped base and of an obtuse angle of each of the two branches with the V-shaped base at the connecting zones is substantially 360°.

8. A plastically deformable surgical clip for end-to-end or end-to-side vascular anastomosis of blood conduits and for suturing blood conduits, made in one-piece of biocompatible material, consisting essentially of a V-shaped base and of two branches which project from the V-shaped base in a direction opposed to an apex of the V-shaped base, wherein the branches each have an internal face and a free end provided with a corresponding hook protruding from the internal face at a distance from the internal face and pointing toward the base for penetrating walls of the blood conduits without perforating said walls, the branches are parallel to one another before plastic deformation and each branch forms with the corresponding hook a re-entrant corner with an apex angle of between 30° and 80°, wherein the clip has three zones of preferential plastic deformation, at the apex of the V-shaped base and at connecting zones between the base and the branches, wherein before deformation, a sum of an angle at the apex of the V-shaped base and of an obtuse angle of each of the two branches with the V-shaped base at the connecting zones is substantially 360°, whereby the clip is plastically deformed by narrowing the apex of the V-shaped base and bringing closer to one another and opening the connecting zones between the base and the branches such that the two branches are brought closer to one another and remain substantially parallel after deformation, wherein the clip is entirely contained between two parallel geometrical planes, each of which contains one end face of the clip, wherein the end face covers the base and the two branches, wherein the internal face of each of the branches is planar and extends between the V-shaped base and the corresponding hook, wherein each of the two branches has a free end and the clip has a height H, measured parallel to the parallel plane faces between the apex and a plane crossing the free end of each of the two branches and perpendicular to the parallel planar end faces, which is between 1 and 5 mm.

* * * * *